Feb. 21, 1967 R. S. MOORE Plant Pat. 2,718
ROSE PLANT
Filed Oct. 11, 1965
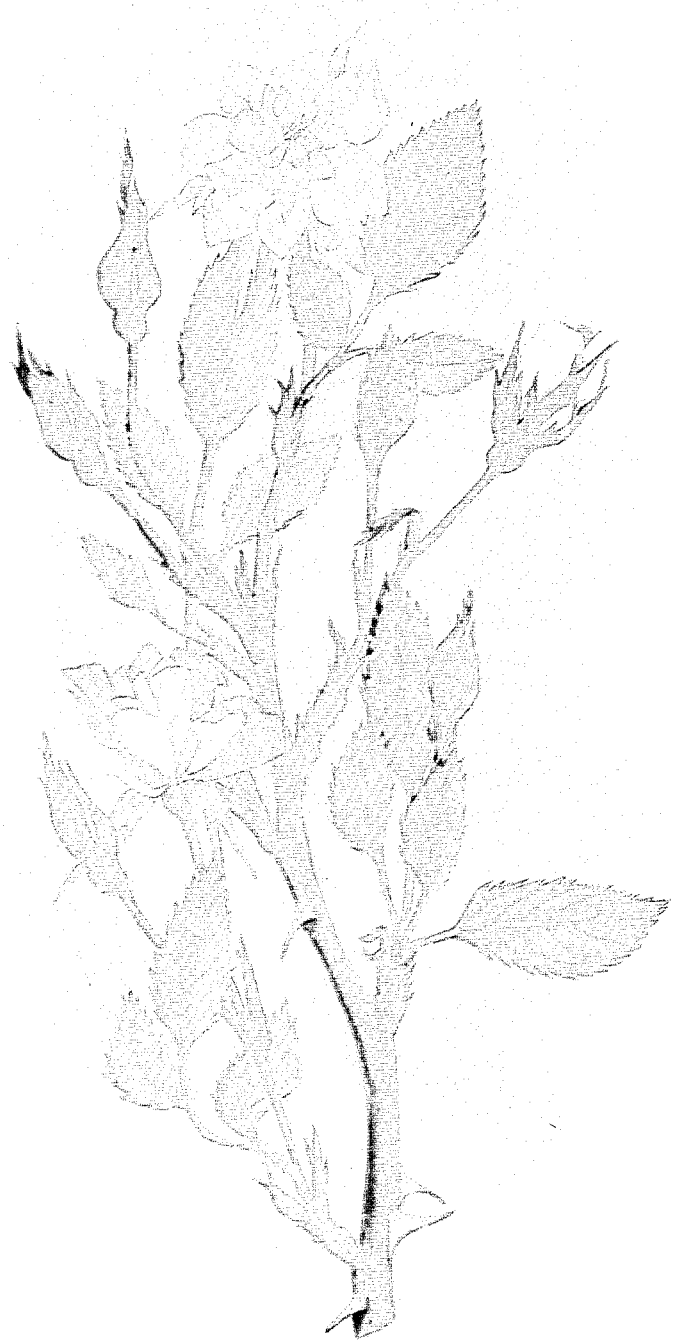
WITNESS
Jeanette Nunn Copley
INVENTOR
Ralph S. Moore

United States Patent Office

Plant Pat. 2,718
Patented Feb. 21, 1967

2,718
ROSE PLANT

Ralph S. Moore, 2519 E. Mineral King,
Visalia, Calif. 93277

Filed Oct. 11, 1965, Ser. No. 494,993
1 Claim. (Cl. Plt.—9)

The present invention relates to a new and distinct variety of hardy, dwarf, bush type rose plant of the hybrid miniature class; the variety being primarily characterized —as to novelty—by rose pink flowers which vary in color according to stage of growth and season of year, but which in general color effect are a bright shade of Tyrian Rose.

The variety is further characterized by:

An abundance of bloom, with flowers borne singly or several to stem. Slight fragrance.

A plant which is moderately vigorous, of low, rounded shape and with semi-glossy, small foliage with pointed leaflets; the flowers being similar in size and shape to the variety Bobolink (Plant Patent No. 2,009). The plant which has a normal height of 9" to 12" at maturity, resembles the general plant habit of New Penny (not patented).

A plant which grows and blooms satisfactorily both in the greenhouse and outdoors; is a good plant for growing in pots; and provides excellent garden decoration as well as cut flowers.

The present variety of miniature rose was originated by me in my nursery located at Visalia, California, under conditions of careful control and observation, as a cross between an unnamed red seedling as the seed parent, and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being of reference to The British Colour Council Horticultural Colour Chart, except where common terms of color definition are employed.

Type: Hardy; dwarf; bush; seedling; greenhouse; outdoors, cut flowers; garden decoration; potted plant.

Class: Miniature

Flowers:

*Continuity.*—Continuous

*Fragrance.*—Slight, sweet

Flowers borne: singly and several together (3–5) on strong, medium length stems.

Quantity of bloom: Abundant—outside and in greenhouse.

Bud:

*Peduncle.*—Medium length; slender, wiry; erect; medium green; often tinted red or bronze; smooth.

*Before calyx breaks.*—Size—small. Form ovoid; small foliaceous appendages on surface of the bud; with foliaceous parts extending beyond the tip of the bud equal to about ½ of its length.

*Color.*—Medium to dark green—sometimes tinted bronze.

*As calyx breaks.*—Color—red.

*As first petal opens.*—Size—small. Form—short—cup (or tulip) shaped. Color—outside—Chrysanthemum Crimson 824/3 with lighter red tones; base yellow; inside—Tyrian Rose 24 with deeper crimson shading; yellow at base.

*Opening.*—Usually opens well.

Bloom:

*Size when fully open.*—Small, averaging 1¼".

*Petalage.*—Very double—35 or more, arranged irregularly.

*Form.*—Nearly flat and full at first, with petals rolled loosely outward, and later at maturity being loosely rolled outward with outer petals often rolled downward, giving flower somewhat of a ball effect.

Petals: Fairly thick; leathery, satiny both inside and outside; often waved along petal edge.

*Shape.*—Outside petals broad lanceolate; intermediate —broad lanceolate; inside—lanceolate.

*Color.*—Newly opened flower from a plant grown outdoors (September 1965), Visalia, California. Outside petal: outside surface—Tyrian Rose 24/1 becoming near white at base with this same color reaching up the center of petal as a narrow line; inside surface—Tyrian Rose 24/1, or darker, shading into near white, then yellow at base. Intermediate petal: outside surface—Rose Bengal 25/1 with irregular white (or near white) stripe running the length of petal; inside surface—Rose Bengal 25/1 with smaller white area running from mid petal into base. Inner petal: outside surface —Rose Bengel 25/1 with white stripe running the length of petal; inside surface—same color with white stripe running the length of petal. Note: Flower colors may often come in lighter shades than indicated above and white stripe may be partially or altogether missing.

*General color effect.*—Newly opened flower—dark rose pink or light rose red. This color effect is often modified by petals being tipped with lighter shades giving effect of a darker colored flower circled or fringed with light pink.

*Behaviour.*—Petals usually drop clean. Petal and flower color may vary considerably at different seasons of the year.

*Flower longevity* (September 1965).—Bush in pot or garden—4 to 6 days. Cut flower kept at living room temperature 3 to 4 days.

Reproductive organs:

*Stamens.*—Few to moderate, often mixed with petaloids.

*Filaments.*—Short, yellow.

*Anthers.*—Small, irregularly shaped, yellow.

*Pollen.*—Scarce.

*Pistils.*—Moderate number.

*Styles.*—Uneven, bunched, red.

*Stigma.*—Lighter shade than styles.

*Ovaries.*—All enclosed in calyx.

*Hips.*—None.

*Sepals.*—Permanent, spear shaped, slightly recurved.

*Seeds.*—None.

Foliage:

*Leaves.*—Compound of five leaflets (sometimes 3); abundant; moderately leathery; semi-glossy.

*Leaflets.*—Shape—broad lanceolate; apex acute; base rounded acute. Margin—serrate. Color—dark green; new growth tinted bronze (much more so than most miniatures). Rachis — medium strength; upper surface grooved with several short hairs; under side sparsely to moderately thorny (small, short thorns). Stipules—moderately long (½" on mature leaf); fairly broad, with numerous hairs along the edges; medium length points, turning out at an angle of about 45 degrees.

Growth:

*Habit.*—dwarf; bushy; often as broad as tall; much branched.

*Growth.*—Vigorous but short and stocky.

*Canes.*—Medium to heavy in proportion to length.

*Main stems.*—Color—medium green. Thorns—moderate; short oval base; medium length; hooked downward. Color—green or green-brown. Prickles—none. Hairs—none.

*Branches.*—Color—medium green. Thorns—moderate; medium length; hooked downward; short oval base. Color—green or green-brown.

*New shoots.*—Color—bright green, often tinted bronze. Thorns—moderately thorny; medium size; hooked downward; short oval base; Color—reddish. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, dwarf, much branched, bush type as illustrated and described, characterized by buds and flowers resembling in form the variety Bobolink (Plant Patent No. 2,009) but having more tendency to vary in color, often with a darker basic flower color (Tyrian Rose 24/1) with petal tips of decidedly lighter shade giving the mature flower a fringe or halo; the overall effect being either a flower of solid light to deep rose color or a flower of deep rose edged with a lighter colored fringe; easy to propagate from cuttings; and further characterized by low, compact growth, the ability to bloom well as a winter potted plant, abundant, healthy, semi-glossy foliage of dark green color with new shoots and foliage often of a decidedly reddish-bronze color, an abundance of bloom, with flowers sometimes borne singly but usually several to stem in loose clusters.

No references cited.

ABRAHAM G. STONE, *Primary Examiner.*

R. E. BAGWILL, *Assistant Examiner.*